United States Patent
Bosman et al.

(10) Patent No.: US 6,747,181 B1
(45) Date of Patent: Jun. 8, 2004

(54) PROCESS FOR THE HYDROGENATION OF PHENYL ACETYLENE IN A STYRENE-CONTAINING MEDIUM WITH THE AID OF A CATALYST

(75) Inventors: Hubertus J. M. Bosman, Sittard (NL); Edwin J. Grootendorst, Born (NL); Leonardus H. Postma, Kerkrade (NL); Theodorus M. Smeets, Elsloo (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/680,308

(22) Filed: Oct. 6, 2000

Related U.S. Application Data

(63) Continuation of application No. PCT/NL99/00245, filed on Apr. 26, 1999.

(30) Foreign Application Priority Data

Apr. 28, 1998 (NL) .............................................. 1009014

(51) Int. Cl.$^7$ .............................................. C07C 7/167
(52) U.S. Cl. ...................... 585/259; 585/258; 585/260; 585/261; 585/262; 585/276
(58) Field of Search ................ 585/258, 259, 585/260, 261, 262, 276

(56) References Cited

U.S. PATENT DOCUMENTS

| | | | | |
|---|---|---|---|---|
| 2,399,514 A | * | 4/1946 | Smoker ...................... | 585/259 |
| 2,511,453 A | * | 6/1950 | Barry .......................... | 585/262 |
| 3,634,531 A | * | 1/1972 | Platz et al. .................. | 585/256 |
| 3,662,015 A | * | 5/1972 | Komatsu et al. ............. | 585/261 |
| 3,793,388 A | * | 2/1974 | Pitzer ......................... | 585/260 |
| 4,734,540 A | * | 3/1988 | Gattuso et al. ............. | 585/260 |
| 5,156,816 A | * | 10/1992 | Butler et al. ................ | 422/141 |
| 5,504,268 A | * | 4/1996 | van der Aalst et al. ..... | 585/259 |
| 6,288,295 B1 | * | 9/2001 | Didillon et al. ............. | 585/260 |

FOREIGN PATENT DOCUMENTS

| | | | |
|---|---|---|---|
| JP | 80035368 | | 9/1980 |
| JP | 63291643 A | * | 11/1989 |

OTHER PUBLICATIONS

A. Okaue; Selective hydrogenation of acetylenes, dienes and olefins; Chemical Abstracts; Sep. 27, 1971; abstract No. 88073h—p. 319.

Y. Nitta; Partial hydrogenation of phenylacetylene on silica–supported iron catalysts; Chemical Abstracts; Mar. 12, 1990; abstract No. 98092k—pp. 547–550.

* cited by examiner

Primary Examiner—Walter D. Griffin
(74) Attorney, Agent, or Firm—Pillsbury Winthrop LLP

(57) ABSTRACT

The invention relates to a process for the hydrogenation of phenyl acetylene in a styrene-containing medium with the aid of a supported nickel catalyst with a nickel content of 10–25 wt. %. This process is by preference used for the hydrogenation of phenyl acetylene in a styrene-containing medium which contains more that 30 wt. % of styrene.

19 Claims, No Drawings

PROCESS FOR THE HYDROGENATION OF PHENYL ACETYLENE IN A STYRENE-CONTAINING MEDIUM WITH THE AID OF A CATALYST

This is a continuation application No. PCT/NL99/00245 filed Apr. 26, 1999.

The invention relates to a process for the hydrogenation of phenyl acetylene in a styrene-containing medium with the aid of a catalyst and in the presence of hydrogen gas.

Styrene is often polymerized to polystyrene. In the styrene-containing medium which is used for this purpose, the phenyl acetylene causes undesirable side reactions during the polymerization, such as cross-linking of the polymer chains. It is therefore of importance to keep the phenyl acetylene content of the styrene-containing medium as low as possible.

The above-mentioned process for the hydrogenation of phenyl acetylene is known from JP-A-55,35368.

Said patent publication describes a process for the hydrogenation of phenyl acetylene in a mixture of styrene, phenyl acetylene and o-xylene with the aid of a palladium or nickel catalyst. In the specific Example hydrogenation is effected with the aid of a palladium catalyst on an alumina carrier.

A drawback of the use of a palladium catalyst is that a palladium catalyst, when used for the hydrogenation of phenyl acetylene in a styrene-containing medium with minor amounts of impurities, rapidly loses its activity and thus has a short service life. This is a major drawback because it entails high catalyst regeneration costs. Further, regeneration of the catalyst means loss of production or the need to have a second reactor which is put on stream while the catalyst is being regenerated in the first reactor.

The aim of the invention is to provide a catalyst which does not present said drawback or only to a lesser extent.

The invention is characterized in that the catalyst is a supported nickel catalyst with a nickel content of 10–25 wt. %. Surprisingly it has appeared now that in a same styrene-containing medium a nickel catalyst is much less sensitive to impurities and thus has a much longer service life. This is all the more surprising in that a person skilled in the art, relying on his knowledge of catalysts, would not be likely to opt for a nickel catalyst instead of a palladium catalyst, since a nickel,catalyst normally has a lower activity and selectivity than a palladium catalyst in the conversion of acetylenes to alkenes (see for instance J. A. Moulijn, P. W. N. M. van Leeuwen and R. A. van Santen, Catalysis, Elsevier, 1993, pp. 180–181).

Further advantages of application of a nickel catalyst are that the price of a nickel catalyst is lower than that of a palladium catalyst and that nickel catalysts are commercially available with a larger catalytically active surface area.

The nickel catalyst applied according to the invention is a supported nickel catalyst. Examples of suitable carrier materials are: silica, $\alpha$-, $\theta$- and $\gamma$-alumina, zeolites, carbon and oxidic carriers, such as for instance magnesium oxide, titanium oxide and zirconium oxide.

Mixtures of different carrier materials can also be used. By preference, $\theta$- and $\gamma$-alumina, silica or carbon are used as carrier material. Particular preference is given to $\theta$- or $\gamma$-alumina as carrier material, because this is an inert carrier material with a large total surface area and a good poor volume distribution.

The nickel catalyst is synthesized for instance in the following way. The nickel is applied onto the carrier material by impregnating it with a solution of nickel salts. Water is commonly used as solvent. Then the impregnated carrier material is dried and subsequently calcinated at elevated temperature. The nickel oxide thus obtained is then activated on the carrier material through a treatment with hydrogen at elevated temperature. A high degree of dispersion of the nickel on the carrier results in a catalyst with a large catalytically active surface area. The higher the catalytically active surface area in the catalyst, the better the phenyl acetylene is hydrogenated.

For economical and technical reasons the nickel content of the nickel catalyst is kept as low as possible. A nickel catalyst with a higher nickel content is more expensive and when the nickel content becomes higher, the dispersion of the nickel in the catalyst is worse.

The nickel content of the catalyst is normally 10–25 wt. %. Supported nickel catalysts are commercially available with for instance 10, 15 or 20 wt. % of nickel. The nickel content of the nickel catalyst preferably is 11 to 25 wt. %.

Most preferably the nickel content of the catalyst is more than 11 and less or equal to 20 wt. %.

Besides the nickel the catalyst can also contain minor amounts of other compounds which enhance the activity and selectivity of the catalyst. Examples of such compounds are: chromium, gold, rhodium and ruthenium. The catalyst can also be modified with sulphur-containing compounds.

When its activity in the hydrogenation of phenyl acetylene has declined strongly, the nickel catalyst can be regenerated. Regeneration is effected for instance by treating the contaminated catalyst with steam and air at a high temperature, for instance 300 to 350° C., followed by reduction with hydrogen at the same temperature. If the catalyst is lightly contaminated it can also be regenerated by merely treating it with hydrogen at an elevated temperature of 100–300° C.

When naphtha, gas condensates and LPG are cracked, cracked petrol is formed. This cracked petrol mainly contains aliphatic and aromatic compounds with 6–9 carbon atoms, including 1–50 wt. % of styrene. Fractionation of this cracked petrol yields a C8 fraction which contains 30–70 wt. % of styrene. When this C8 fraction is extracted with a solvent and then distilled, a styrene-rich fraction is obtained which may contain more than 95 wt. % of styrene. The cracked petrol, the C8 fraction as well as the styrene-rich fraction can be used as styrene-containing medium.

A styrene-containing medium can also be obtained by means of chemical synthesis. Alkylation of benzene with ethene gives ethyl benzene, which through dehydrogenation can be converted into a styrene-containing medium which besides styrene can also contain ethyl benzene and phenyl acetylene.

The invention is not restricted, however, to the hydrogenation of phenyl acetylene in the above-mentioned styrene-containing media. Styrene-containing media which have been obtained in another way can also be employed.

The styrene-containing media can comprise up to 99.99 wt. % of styrene.

The styrene-containing medium preferably comprises more than 30 wt. % of styrene. By particular preference, the styrene-containing medium is a C8 hydrocarbon fraction which comprises more than 30 wt. % of styrene.

In the hydrogenation of phenyl acetylene in the styrene-containing medium it is preferred for all phenyl acetylene in the styrene-containing medium to be converted to styrene or ethyl benzene, with a limited amount of phenyl acetylene or styrene being hydrogenated to ethyl benzene.

The phenyl acetylene content of a styrene-containing medium is normally between 0.01 and 5 wt. % relative to the styrene present in the styrene-containing medium. During the hydrogenation process according to the invention this content is reduced. Said content is preferably reduced to less than 100 ppm, by particular preference to less than 10 ppm in the styrene-containing medium.

The process for the hydrogenation of phenyl acetylene in a styrene-containing medium is carried out in a reactor. The catalyst on a support is present in the reactor. The reactor is fed with the styrene-containing medium and hydrogen gas. The hydrogen gas can optionally have been diluted with another, inert gas such as for instance nitrogen gas. The styrene-containing medium and the hydrogen gas can be mixed before being fed to the reactor.

The reactor can be operated as a two-phase or as a three-phase reactor.

If the reactor is operated as a two-phase reactor, then the hydrogen gas that is required for the At hydrogenation of the phenyl acetylene is fully dissolved in the styrene-containing medium that is supplied to the reactor.

If the reactor is operated as a three-phase reactor the styrene-containing medium and the hydrogen gas are fed in at the bottom of the reactor and the product is obtained at the top of the reactor. It is also possible to supply the styrene-containing medium and the hydrogen gas at the top of the reactor and to recover the product at the bottom of the reactor. The reactor can also be operated as a countercurrent reactor, with for instance the hydrogen gas being supplied at the bottom of the reactor and the styrene-containing medium at the top. The product is recovered at the bottom of the reactor.

By preference the styrene-containing medium and the hydrogen gas are supplied at the bottom of the reactor, because there is less backmixing then and thus less styrene and phenyl acetylene react further to form ethyl benzene.

The nickel catalyst is preferably present in a fixed bed in the reactor. The styrene-containing medium and the hydrogen gas are contacted with this fixed bed.

A fixed bed is a bed of solid catalyst parts that can have different shapes and can be, for instance, granules, pellets, extrudates, spheres, triloops and qaudruloops. The fixed bed can also consist of a monolith or of miniliths.

The hydrogen pressure in the reactor is usually between 0 and $300.10^5$ Pa overpressure, preferably between 0 and $50.10^5$ Pa overpressure. Preferably a low pressure is applied, because then the reactor does not have to have a thick wall and is therefore less costly.

The temperature is usually between 0 and 100° C., preferably between 15 and 50° C. If the temperature rises above 50° C., polymerization of styrene occurs during the reaction.

The process according to the invention is preferably carried out with a hydrogen: phenyl acetylene molar ratio ≦1. By preference this molar ratio is between 1 and 10. For commercial-scale applications this molar ratio is preferably between 1 and 4. The molar ratio is kept as low as possible in order to prevent conversion of styrene and phenyl acetylene into ethyl benzene.

The average residence time of the styrene-containing medium in the reactor should not be too long, because hen more styrene and/or phenyl acetylene react(s) further to ethyl benzene. The average residence time should not be too short either, because then the degree of conversion of phenyl acetylene to styrene is too low. A measure for the average residence time is the liquid hourly space velocity (LHSV).

The process according to the invention is usually carried out with a LHSV of between 0.1 and 100 per hour, preferably between 1 and 10 per hour.

The invention will now be elucidated by means of examples, without being restricted thereto.

EXAMPLES

Example I

A reactor with a capacity of 1 m³ was completely filled with a fixed bed consisting of a nickel catalyst on θ-alumina. The catalyst contained 15 wt. % of nickel.

A C8 fraction comprising 50 wt. % of styrene, 8 wt. % of ethyl benzene and 0.8 wt. % of phenyl acetylene was supplied to the bottom of this reactor. Hydrogen gas was also supplied to the bottom of the reactor, the hydrogen gas:phenyl acetylene molar ratio being kept between 2 and 3. The LHSV was 4 h⁻¹ and the contact time was 15 minutes.

Further data of the reaction are presented in Table 1. The data were registered after different on-stream times of the reactor. Measurements were carried out after 10, 100 and 220 days.

Comparative Example A

In the reactor of example I a hydrogenation reaction was carried out with a palladium catalyst instead of a nickel catalyst. A palladium catalyst on γ-alumina containing 0.2 wt. % of palladium was used. The other reaction conditions were the same as in example I. The service life of this catalyst was only 10 days. After 10 days the degree of conversion of phenyl acetylene had declined to the point where continuation of the hydrogenation reaction with this catalyst was not sensible any more.

Further data of the reaction are presented in Table 1.

Example II

In the reactor of Example I a hydrogenation reaction was carried out with the catalyst according to Example I after regeneration. The catalyst was regenerated by treating it with steam and air at 300° C., followed by reduction with hydrogen at the same temperature.

The LHSV was 6 hr⁻¹ and the contact time was 10 minutes. The other reaction conditions were the same as in Example I.

Data after different on-stream times of the reactor were registered. Measurements were carried out after 10 and 100 days. Further data of the reaction are presented in Table 1.

TABLE 1

| Example | t (days) | $T_{in}$ (° C.) | $T_{out}$ (° C.) | $\Delta T$ (° C.) | $X_{ph}$ (%) | $Ph_{out}$ (ppm) |
|---|---|---|---|---|---|---|
| I | 0 | 28 | 46 | 18 | 99.8 | <10 |
|   | 10 | 28 | 46 | 18 | 99.8 | <10 |
|   | 100 | 34 | 49 | 15 | 99.7 | <20 |
|   | 220 | 39 | 53 | 14 | 99.6 | <30 |
| A | 0 | 20 | 40 | 20 | 99.9 | <10 |
|   | 10 | 22 | 28 | 6 | 75.0 | 200–300 |
| II | 0 | 30 | 45 | 15 | 99.8 | <10 |
|   | 10 | 30 | 45 | 15 | 99.6 | <10 |
|   | 100 | 35 | 48 | 13 | 98.9 | 100 |

Explanation of the symbols:
t = time
$T_{in}$ = inlet temperature of the styrene-containing medium
$T_{out}$ = outlet temperature of the styrene-containing medium
$\Delta T$ = difference between the inlet and the outlet temperature
$X_{ph}$ = conversion of phenyl acetylene
$Ph_{out}$ = the phenyl acetylene content of the styrene-containing medium leaving the reactor

Example III

A 95 ml reactor was filled with a fixed bed of 70 ml consisting of nickel catalyst on θ-alumina. The catalyst contained 15 wt. % of nickel.

At the bottom of the reactor a C8 fraction was supplied, containing 50 wt. % of styrene, 8 wt. % of ethyl benzene and 0.8 wt. % of phenyl acetylene. The LHSV was 5 hr$^{-1}$, the hydrogen pressure was 3 bar and the inlet temperature was 40° C. Hydrogen gas was also supplied via the reactor bottom, with a varying hydrogen gas/phenyl acetylene molar ratio, as indicated in Table 2. From Table 2 it appears that at a higher hydrogen gas/phenyl acetylene molar ratio the conversion of phenyl acetylene increases. Some styrene is reacted further to ethyl benzene, however, causing the net styrene yield to decrease a little again.

Example IV

Example III was repeated, using a nickel catalyst on θ-alumina containing 20 wt. % of nickel instead of 15 wt. %. The inlet temperature was 30° C. The other reaction conditions were the same as in Example III. Hydrogen gas was supplied via the reactor bottom, with a varying hydrogen gas/phenyl acetylene molar ratio, as indicated in Table 2. From Table 2 it appears that at a higher nickel content of the catalyst the same degree of conversion of phenyl acetylene is obtained with a lower hydrogen/phenyl acetylene molar ratio. From this example it also appears that when the hydrogen/phenyl acetylene molar ratio is too high, styrene is also hydrogenated.

TABLE 2

| Example | H$_2$/ph (mol/mol) | X$_{ph}$ (%) | S (%) |
|---|---|---|---|
| III | 3 | 98.5 | 0.3 |
|  | 5 | 99.9 | 0.1 |
|  | 7 | 99.9 | 0.1 |
| IV | 1 | 91 | 0.4 |
|  | 2 | 99.9 | 0.2 |
|  | 3 | 99.9 | −0.2 |

Explanation of the symbols:
X$_{ph}$ = conversion of phenyl acetylene
H$_2$/ph = molar ratio hydrogen/phenyl acetylene
S = net styrene yield in the medium leaving the reactor relative to the medium supplied to the reactor Example V Example III was repeated at elevated temperature and with a LHSV of 5.5 hr$^{-1}$. At a temperature of 70° C. the conversion of phenyl acetylene was 94% at the start of the experiment. After 5 days the conversion of phenyl acetylene had declined to 30%.

At a temperature of 90° C. the conversion of phenyl acetylene was 100% at the start of the experiment. After 4 days the conversion of phenyl acetylene had declined to 40%.

The strong decline of the conversion of phenyl acetylene is due to formation of polystyrene on the catalyst surface at higher temperatures, resulting in loss of catalyst activity.

What is claimed is:

1. Process for the hydrogenation of phenyl acetylene in a styrene-containing liquid medium with the aid of a catalyst and in the presence of hydrogen gas, wherein the catalyst is a sulfur-free nickel catalyst with a nickel content of 10–25 wt. %, supported on a carrier material and wherein the hydrogenation is carried out at a temperature between about 15 and about 50° C. and an hydrogen pressure between 1 and 30 bar.

2. Process according to claim 1, wherein the nickel content of the catalyst is 11–25 wt. %.

3. Process according to claim 1, wherein the carrier material is θ- or γ-alumina.

4. Process according to claim 1, wherein the catalyst is a fixed-bed catalyst with which the styrene-containing medium and the hydrogen gas are contacted.

5. Process according to claim 1, wherein the styrene-containing medium and the hydrogen gas are supplied at the bottom of a reactor.

6. Process according to claim 1, wherein the hydrogen gas/phenyl acetylene molar ratio is 1–4.

7. Process according to claim 1, wherein the phenyl acetylene content of the styrene-containing medium is 0.01–5 wt. %.

8. Process according to claim 1, wherein hydrogenation is carried out at an LHSV between 0.1 and 100 per hour.

9. Process according to claim 1, wherein hydrogenation is carried out at an LHSV between 0.1 and 10 per hour.

10. Process according to claim 1, wherein the styrene-containing medium contains ≧30 wt. % of styrene.

11. Process according to claim 1, wherein the styrene-containing medium is a C8 hydrocarbon fraction containing ≧30 wt. % of styrene.

12. Process according to claim 1, wherein the catalyst further comprises chromium, gold, rhodium or ruthenium.

13. Process according to claim 1, which further comprises carrying out the hydrogenation reaction for up to about 100 days without regeneration of the catalyst.

14. Process according to claim 1, which further comprises regenerating the catalyst after it becomes contaminated resulting in a decline in hydrogenation activity.

15. Process according to claim 14, wherein said regenerating comprises treating the contaminated catalyst with steam and air at an elevated temperature, followed by reduction with hydrogen at the elevated temperature.

16. Process according to claim 1, wherein the amount of phenyl acetylene in the styrene-containing medium following hydrogenation, is less than about 100 ppm.

17. Process according to claim 1, wherein the amount of phenyl acetylene in the styrene-containing medium following hydrogenation, is less than about 10 ppm.

18. Process according to claim 1, which further comprises carrying out the hydrogenation reaction for up to about 220 days without regeneration of the catalyst.

19. Process according to claim 1, wherein the hydrogen gas/phenyl acetylene molar ratio is 1–10.

* * * * *